(12) United States Patent
Shafee et al.

(10) Patent No.: US 8,999,384 B2
(45) Date of Patent: Apr. 7, 2015

(54) IMMEDIATE RELEASE COMPOSITIONS OF ACID LABILE DRUGS

(76) Inventors: Muneera Mohamed Shafee, Jeddah (SA); Ruckmani Kandasamy, Tiruchirapalli (IN); Thusleem Omar Abdulgani, Jeddah (SA); Saleem Zainuddin Shaikh, Jeddah (SA); Anand Vasantharao Kondaguli, Jeddah (SA)

( * ) Notice: Subject to any disclaimer, the term of this patent is extended or adjusted under 35 U.S.C. 154(b) by 237 days.

(21) Appl. No.: 12/987,367

(22) Filed: Jan. 10, 2011

(65) Prior Publication Data

US 2011/0171295 A1     Jul. 14, 2011

Related U.S. Application Data

(60) Provisional application No. 61/293,926, filed on Jan. 11, 2010.

(51) Int. Cl.
  *A61K 9/20*      (2006.01)
  *A61K 31/4439*   (2006.01)
  *A61K 9/48*      (2006.01)
  *A61K 9/50*      (2006.01)
  *A61K 9/28*      (2006.01)

(52) U.S. Cl.
  CPC .............. *A61K 31/4439* (2013.01); *A61K 9/20* (2013.01); *A61K 9/2018* (2013.01); *A61K 9/2013* (2013.01); *A61K 9/2009* (2013.01); *A61K 9/2086* (2013.01); *A61K 9/4808* (2013.01); *A61K 9/5084* (2013.01); *A61K 9/2813* (2013.01)

(58) Field of Classification Search
  CPC ..... A61K 9/20; A61K 9/2004; A61K 9/2009; A61K 9/2013; A61K 9/2018
  USPC ......................................................... 424/464
  See application file for complete search history.

(56) References Cited

U.S. PATENT DOCUMENTS

| 6,489,346 | B1 | 12/2002 | Phillips |
| 2003/0235628 | A1* | 12/2003 | Taneja et al. .................. 424/687 |
| 2006/0204585 | A1* | 9/2006 | Hall et al. ..................... 424/489 |
| 2007/0020334 | A1* | 1/2007 | Bertelsen et al. ............. 424/472 |
| 2007/0259040 | A1 | 11/2007 | Ishida et al. |
| 2009/0092658 | A1 | 4/2009 | Hall et al. |

FOREIGN PATENT DOCUMENTS

| EP | 1 854 463 A1 | 11/2007 |
| WO | WO 03/024449 A1 | 3/2003 |
| WO | WO 2006/031256 A1 | 3/2006 |

OTHER PUBLICATIONS

Small, Ralph E., "Advances in Proton Pump Inhibitor Therapy: An Immediate-Release Formulation of Omeprazole," p. 698-702, 711-713 *P&T* (Dec. 2005 vol. 30 No. 12).

* cited by examiner

*Primary Examiner* — Ali Soroush
(74) *Attorney, Agent, or Firm* — Brinks Gilson & Lione; Ryan L. Marshall

(57) ABSTRACT

The present invention provides a method of creating a macro environment in the stomach for immediate release of acid labile compounds stable at alkaline or near alkaline pH comprising the step of administering a composition comprising acid labile compound stable at alkaline or near alkaline pH together with a water soluble buffer, a water insoluble buffer, a disintegrant and pharmaceutically acceptable excipients. The present invention also provides a pharmaceutical composition of a multi component system in which one component essentially contains an acid labile drug and the other component comprises a fast releasing buffer composition along with pharmaceutically acceptable excipients for oral administration and ingestion by a subject, and process for preparing the same.

34 Claims, 4 Drawing Sheets

Figure 6: Geometric Mean Plasma Concentration (μg/ml) versus time (hours) curves of Pantoprazole 40 mg (T= PANTOPRAZOLE and R= PANTOZOL®) based on 12 participants.

IMMEDIATE RELEASE COMPOSITIONS OF ACID LABILE DRUGS

REFERENCE TO EARLIER FILED APPLICATION

This application claims the benefit under 35 U.S.C. §119 (e) of U.S. Provisional Patent Application No. 61/293,926, filed Jan. 11, 2010, and titled "IMMEDIATE RELEASE COMPOSITIONS OF ACID LABILE DRUGS," which is incorporated, in its entirety, by this reference.

BACKGROUND

1. Technical Field

The present invention relates to method for creating a macro environment of buffers for delivering acid labile pharmaceuticals, stable at alkaline or near alkaline pH and oral pharmaceutical compositions of acid labile drugs, stable at alkaline or near alkaline pH and process for the preparation of the same in pharmaceutically acceptable dosage forms.

2. Background Information

Acid labile drugs such as the proton pump inhibitors tend to be unstable at acidic pH and therefore have to be formulated as enteric-coated dosage forms to prevent acid degradation. Although these drugs are stable at alkaline pH, they are destroyed rapidly as pH falls (for example, by gastric acid). Or, if the enteric-coating of the composition is disrupted (for example by chewing) resulting in degradation of the active ingredient by the gastric acid in the stomach. Upon ingestion, an acid-labile pharmaceutical compound must be protected from contact with acidic stomach secretions to maintain its pharmaceutical activity. Certain acid labile drug compositions with enteric-coating have been designed to dissolve at basic or near neutral pH to ensure that the drug is released in the proximal region of the small intestine (duodenum), not in the stomach. However, due to their pH-dependent attributes and the uncertainty of gastric retention time, in-vivo performances as well as inter and intra subject variability are very high; making it an uncertain method. Nevertheless at basic/near neutral pH also most acid-labile pharmaceutical agents are still susceptible to degradation depending on the particular pKa of the agent. Further as an acid-labile compound upon ingestion must be transferred in intact form, i.e., a non-acid degraded or reacted form, to the duodenum where the pH is near or above its pKa, the enteric-coating must be resistant to dissolution and disintegration in the stomach, that is, be impermeable to gastric fluids while residing in the stomach. Additionally, since the therapeutic onset of an enteric-coated dosage form is largely dependent upon gastric emptying time it varies between subjects. In most subjects, gastric emptying is generally an all or nothing process, and generally varies from about 30 minutes to several hours after ingestion. Thus, for a period of time following ingestion, an enteric-coated dosage form resides in the low pH environment of the stomach before moving into the duodenum. During this time, the enteric-coating may begin to dissolve, or imperfections or cracks in the coating may develop, allowing gastric acid to penetrate the coating and prematurely release drug into the stomach rather than in the small intestine. In the absence of buffering agent, an acid-labile drug that is exposed to this gastric acid is rapidly degraded and rendered therapeutically ineffective.

To overcome the disadvantages of gastric emptying time; Enteric-coated dosage forms are generally taken on an empty stomach with a glass of water. This minimizes exposure time to gastric fluid, as it ensure gastric emptying within about 30 minutes or so, and delivery of the dosage form from the stomach to the duodenum. Once in the duodenum, optimal conditions exist for the enteric-coating to dissolve and release the drug into the bloodstream where absorption of a non-acid degraded drug occurs. If food is ingested contemporaneously with the administration of an enteric-coated dosage form, gastric emptying may not only be slowed, but there is also an increase in the pH of the stomach from about pH 1 to about 5 over the next several hours, depending on, for example, the general health of the subject and the composition being administered. When the pH begins to approach 5, the enteric-coating begins to dissolve away resulting in premature release of the drug into the stomach.

In geriatric patients the gastric pH is already elevated as there is a general decline in gastric acid secretion in the stomach with aging. In such patients; enteric coated acid labile drugs are less effective. Also, when the ingested food contains any fat, gastric emptying can be delayed for up to 3 to 6 hours or more, as fat in any form combined with bile and pancreatic fluids strongly inhibits gastric emptying. Thus, as a general rule, enteric-coated dosage forms should only be ingested on an empty stomach with a glass of water to provide optimal conditions for dissolution and absorption.

To overcome the problems of enteric coated tablets; several scientists used compositions comprising large amounts of buffers (U.S. Pat. No. 6,489,346 B1, 03/2002 Jeffrey Owen Philips et al.) to prevent the degradation of acid labile drugs.

For instance, certain compositions of omeprazole contain 1100 mg of sodium bicarbonate (equivalent to 300 mg of sodium) and oral suspension contains 1680 mg of sodium bicarbonate (equivalent to 460 mg of sodium). Such formulations utilizes the concept of microenvironment pH and hence a large quantity of alkali is required to neutralize the acid in the stomach so as to protect the uncoated PPI from acid degradation and maintain intragastric pH>4 for a period of about 18 hours. The American Heart Association's recommended daily intake of sodium is 2,400 mg for a normal person and, these amounts should be taken into consideration by anyone on a sodium-restricted diet. Also Sodium bicarbonate is contraindicated in patients with metabolic alkalosis and hypocalcemia. Also such compositions weigh about 1.5-2.0 g making it difficult to swallow and hence leading to patient non-compliance. Furthermore, since, the amount of buffer depends on the pKa of the drug used, the amount of alkali required to make an immediate release composition of Pantoprazole or Rabeprazole, may be more than that required for Omeprazole. Moreover, sodium bicarbonate used in the composition has poor stability properties and decomposes by converting to carbonate and such; the decomposition is accelerated by agitation or heat. Hence, such compositions comprising large amount of buffers are also not suitable for long term usage.

All the compositions of prior art are based on the concept of micro environmental pH which is also known as virtual pH. The micro environmental or virtual pH can be said as the pH of the immediate solution when the solid is dissolved in water. This virtual membrane pH determines the extent of drug ionization and hence drug dissolution and absorption. Thus the concept of microenvironment pH questions the basics of pH partition hypothesis. It has been demonstrated that the pH of the diffusion layer at the surface of the dosage form resembles that of a saturated solution of drug and excipients in a dissolution media and represents the microenvironment pH of the system. During dissolution, medium that may eventually penetrate into the core, or during storage moisture may penetrate into the core resulting in a saturated solution of drug and excipients. If the microenvironment pH is low, it will lead to ultimate degradation of the drug.

Hence; it is seen that the compositions of acid labile drugs of prior art either use an enteric coating or high concentration of buffers or are liable to degradation in the microenvironment pH.

Therefore, there needs to be an effective method for delivering acid labile drugs such that the acid labile drugs do not degrade in the stomach.

Also, there is a need for a stable and robust composition of an immediate release composition for acid labile drugs, that is not enteric coated, uses minimal amount of buffer and it is not susceptible to degradation by acid labile drugs.

3. Object of the Invention

An object of the invention is to create a macro environment having a pH of 5 to 10 in the stomach for immediate release of acid labile compounds stable at a pH between 5 to 10.

Another object of the invention is to provide an immediate release composition of acid labile drugs that use the concept of a macro-environment pH instead of a micro-environment pH.

Yet another object of the present invention is to provide an immediate release stable pharmaceutical composition of acid labile drugs or its pharmaceutically acceptable salts and process for preparing the same.

Yet another object of the invention is to provide a composition that eliminates need for enteric coating and use of high concentration of buffers.

A further object of the invention is to provide a process for preparing the composition.

BRIEF SUMMARY

The present invention provides a method of creating a macro environment of buffers in the stomach for immediate release of acid labile compounds stable at alkaline or near alkaline pH comprising the step of administering a composition comprising an acid labile compound stable at alkaline or near alkaline pH together with a water soluble buffer, a water insoluble buffer, a disintegrant and pharmaceutically acceptable excipients. The present invention also provides a pharmaceutical composition of a multi component system in which one component comprises a core composition that essentially contains an acid labile drug stable at alkaline or near alkaline pH and the other component comprises a fast releasing buffer composition along with pharmaceutically acceptable excipients for oral administration and ingestion by a subject, and process for preparing the same.

DETAILED DESCRIPTION OF THE DRAWINGS AND THE PRESENTLY PREFERRED EMBODIMENTS

Figure 1A:
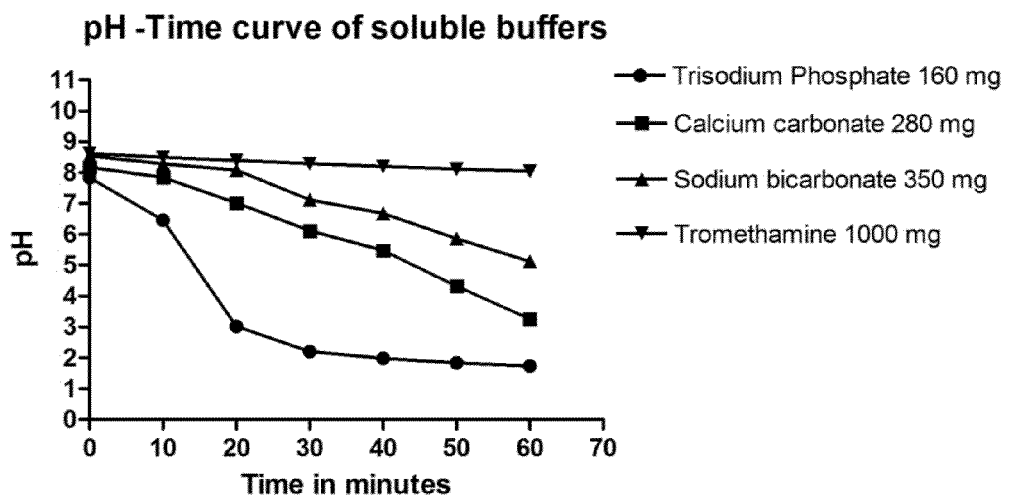
FIGS. 1a through 1c illustrate the comparative pH time curve of different buffers.

Accordingly the invention provides a method of creating a macro environment pH in the stomach for immediate release of acid labile compounds stable at alkaline or near alkaline pH comprising the step of administering a composition comprising an acid labile compound stable at alkaline or near alkaline pH together with a water soluble buffer, a water insoluble buffer, a disintegrant and pharmaceutically acceptable excipients.

An alkaline or a near alkaline pH is in the pH range of 5 to 10.

The disintegration of the composition of the present invention begins within 15 minutes; more preferably, the disintegration begins within 4 minutes. The method of the present invention creates a macro environment with a pH of 5 to 10 within 20 minutes after disintegration of the composition, more preferably within 15 minutes and most preferably within 10 minutes or less. The created macro environment is maintained above 5 for 15 minutes, preferably for 30 minutes, and more preferably for 60 minutes.

The acid labile compound is released from the composition within 30 minutes, more preferably within 15 minutes and most preferably within 10 minutes or less after disintegration of the composition. The dissolution rate of the composition of the present invention is about 95% within 15 minutes and about 100% in 30 minutes.

The acid labile compound may be simultaneously co-administered with the buffers as a separate formulation. However, it is preferred that the buffer may be administered along with the acid labile compound in a same composition.

Oral dosage forms suitable for co-administration of the buffer along with the acid labile compound include but are not limited to inlay tablet, inlay caplet, multilayered tablet, multilayered caplet, mixture of pellets compressed into tablet, mixture of pellets filled into capsule, pellets and granules compressed into tablet, mini tablets filled into capsule, tablet and powder filled into capsule, tablet and granular powder filled into capsule, pellets and powder filled into capsule, pellets and granular powder filled into capsule.

Accordingly the present invention provides a pharmaceutical composition for immediate release oral compositions of acid labile drugs.

The composition of the present invention comprises an acid labile compound stable in alkaline or near alkaline pH, a water soluble buffer, a water-in soluble buffer, a disintegrant and pharmaceutically acceptable excipients.

The composition may be present as a multi component system in which one component is a core composition that essentially contains the therapeutic agent or comprising an acid labile drug and the other component is a fast releasing buffer composition along with pharmaceutically acceptable excipients.

The acid labile compound is selected from the group comprising prazoles, stable in alkaline or near alkaline pH, as free base, free acid, salt, hydrate, polymorph or prodrug thereof. The alkali soluble drugs is selected from the group comprising COX-2 inhibitors; antidiabetics; retinoids and other drugs soluble at alkaline or near alkaline pH as free base, free acid, salt, hydrate, polymorph or prodrug thereof.

The acid labile compound of the present invention may be omeprazole, pantoprazole, rabeprazole, esomeprazole, lansoprazole and other such drugs belonging to the group of prazoles.

The drugs soluble at alkaline or near alkaline pH also include compounds selected from the group comprising COX-2 inhibitors such as Etoricoxib, Nimesulide; antidiabetics like Glimepiride; retinoids like Isotretinoin. The active ingredient may be present as their free base, free acid, salt, hydrate, polymorph or prodrug thereof.

The composition of the present invention also includes a buffer. The term buffer as used herein means any compound or combination of compounds that increase the pH of the environment in which they are dissolved or dispersed. Both water soluble and water insoluble buffers or a combination of both can be used. Water soluble buffers may be selected from the group comprising meglumine, sodium bicarbonate, sodium carbonate, sodium citrate, calcium gluconate, disodium hydrogen phosphate, dipotassium hydrogen phosphate, tripotassium phosphate, sodium tartrate, sodium acetate, calcium glycerophosphate, tromethamine and preferably, trisodium phosphate or any combination of the foregoing. "Water-insoluble buffers" could be selected from the group comprising magnesium hydroxide, aluminum hydroxide, dihydroxy aluminum sodium carbonate, calcium carbonate, calcium hydroxide, aluminum phosphate, aluminum carbonate, dihydroxy aluminum amino acetate, magnesium oxide magnesium trisilicate, magnesium carbonate, and combinations of the foregoing. Most preferably, the water insoluble buffer is Magnesium oxide.

It is preferred that the composition of the present invention comprises a combination of buffers from the class of water-insoluble and water soluble buffers, however combinations within the class and also use of single buffers are envisaged within the scope of this invention. Most preferably, the quantity of water-soluble buffer in the formulation is between 50 mg and 1000 mg, preferably between 100 mg and 600 mg, and more preferably between 200 mg and 500 mg. The quantity of water-insoluble buffer in the formulation is typically between 50 mg and 1000 mg, preferably between 100 mg and 500 mg, and more preferably between 100 mg and 300 mg. The total amount of buffer in the formulation with that of the active ingredient could be in the range preferably between 1:20 to 1:15, more preferably between 1:15 to 1:13 and most preferably between 1:12 to 1:10.

The fast releasing buffer composition of the present invention also comprises disintegrants. The disintegrant of the present invention does not include super disintegrants such as crocarmellose sodium, crospovidone or sodium starch glycolate. It has been observed by the inventors that contrary to prior art; super-disintegrants decrease the dissolution rate in an acidic medium. Hence the inventors have formulated this novel composition; in the absence of superdisintegrants. The disintegrants of the present invention are selected from polyols or sugars or a mixture of both polyol and sugars. Examples of polyols suitable for composition of the present invention include but are not limited to mannitol, sorbitol, xylitol, lactitol, erythritol or maltitol or combination thereof. Examples of sugars suitable for composition of the present invention include sucrose, special grade sucrose of commercially available brands like Alveo sugar from Tate & Lyle, castor sugar, icing sugar. Preferably the disintegrant of the present invention is mannitol, which includes commercial brands such as Mannitol M 25 from Roquette, France or Mannogem from SPI Pharma, Compressol M from SPI Pharma or other such mannitols. In general, the amount of disintegrates, contained in the fast releasing buffer composition is in the range of 5% to 50% w/w, more preferably is in the amount of 5% to 40% w/w and most preferably 5% to 25% w/w of the total composition.

The core composition of present invention may optionally include other pharmaceutically acceptable excipients such as preferably a stabilizing agent, pharmaceutical acceptable fillers like microcrystalline cellulose, hydroxyl propyl cellulose, pregelatinised starch like starch 1500, mannitol, ludipress, lactose, binders, tablet lubricant, glidants and other pharmaceutically acceptable excipients.

The core composition of the present invention includes cellulose derivatives like hydroxy propyl cellulose, microcrystalline cellulose, modified starches such as starch 1500, various polyols like mannitol, sorbitol xylitol, lactitol, erythritol or maltitol either alone or in combination thereof. Preferably, filler is used in an amount of about 20-55% by weight of the composition.

The core composition of the present invention may additionally comprise lubricants such as calcium stearate, magnesium stearate, zinc stearate, glyceryl behenate, polyethylene glycol, sodium stearyl fumarate, stearic acid, and talc. The preferred lubricant is magnesium stearate. Preferably, lubricant is used in an amount of 0.2-5% by weight of the composition.

The core composition of the present invention may also comprise a binder such as hydroxypropyl cellulose, polyvinylpyrrolidone, and methylcellulose. Hydroxypropyl cellulose is commercially available under the brand name Klucel EXF Pharm from Aqualon-Hercules, USA. The preferred optional binder for the composition of the present invention is hydroxypropyl cellulose. Preferably, the binder is used in amounts of about 0.5-5% by weight of the composition.

In addition the core composition of the present invention may comprise glidants such as calcium silicate, magnesium silicate, colloidal silicon dioxide and talc. The preferred glidant is colloidal silicon dioxide. Preferably the glidants are used in amounts of about 0.2-5% by weight of the composition.

The core composition of the present invention may be formulated such that the core may be of an acid labile active ingredient, wherein said core comprises of, by weight: about 1 to 45% of active ingredient, and further comprises of about 25 to 55% of a filler, optionally about 2 to 15% of an alkaline agent, wherein the alkaline agent is salts of alkaline earth metals like sodium carbonate or calcium carbonate or magnesium hydroxide or magnesium oxide or calcium hydroxide but not limited to any of the mentioned; about 1 to 8% of a disintegrant, where in the disintegrant is crospovidone NF or low substituted hydroxyl propyl cellulose but not limited to any of the mentioned, about 0.5 to 2% of a binder, about 0.2 to 3% of a lubricant, about 0.2 to 2% of a glidant. The composition may further comprise about 2 to 55% of high molecular weight polymers like PEG 4000, PEG 6000, PEG 8000, PEG 16000; or any block polymers like poloxamer.

In another aspect, the composition of the present invention is suitable for oral administration. Solid oral dosage forms of the present invention may also be coated with any coating as known in the art, preferably with a seal or seal coating layer, but essentially devoid of enteric coating.

The composition of the present invention may be prepared by melt granulation or melt congealing or spray congealing method or any other methods known in the art, for the preparation of the said solid oral dosage form.

In yet another aspect of the invention, the oral dosage form comprising the composition of the present invention is prepared by a process wherein
 a. The buffer of the composition is released first;
 b. The buffer achieves a pH of 5 to 10 in the stomach;
 c. The active ingredient is released after the pH of 5 to 10 is achieved.

Suitable dosage forms of oral administration include but are not limited to inlay tablet, inlay caplet, multilayered tablet, multilayered caplet, mixture of pellets compressed into tablet, mixture of pellets filled into capsule, pellets and granules compressed into tablet, mini tablets filled into capsule, tablet and powder filled into capsule, tablet and granular powder filled into capsule, pellets and powder filled into capsule, pellets and granular powder filled into capsule. Preferably the composition of the present invention is formulated as inlay tablets; tablet and granular powder filled in a capsule; pellets and granular powder filled in a capsule.

In another aspect of the invention, the dosage form of the present invention is packaged in metal-metal packaging component like aluminium-aluminium blisters, strips, sachet, pouch, glass bottle with metal caps, glass bottle with metal seal so as to effectively prevent moisture absorption.

Without being limited by the concept, the composition of the invention disintegrates immediately, due to the use of highly soluble sugars as disintegrants, thereby releasing the buffers. Due to the novel combination of the buffers in the composition, certain component of the buffer causes an initial rise in the pH. The rise in the pH is sustained by the other component of the buffer. Hence, the pH is maintained in a macro-environment as opposed to the micro-environmental pH adjustment of prior art compositions. Followed by the change in pH, the active ingredient is released at the site with immediate effect causing an enhanced therapeutic benefit to the patient. It is further observed that composition of the present invention can be used for acid labile drugs irrespective of the pKa of the drug.

The invention is illustrated by the following examples which are only meant to illustrate the invention and not act as limitations. All embodiments apparent to a person skilled in the art are deemed to fall within the scope of the present invention.

EXAMPLES

Example 1

Selection of Buffer

A number of buffers, both soluble and insoluble, were tested for their acid neutralizing capacity. Based on their acid neutralizing capacity, buffers, both individual and combination, were evaluated for their behavior at the excess secretion of acid. The technique involved consists of adding an excess dose of the buffer to a sample of artificial gastric juice. The basal stomach fluid contains 9.6 ml of 0.1N HCl and releases 0.5 ml of 0.1N HCl per minute (C. Lentner. Basle, CIBA GEIGY, Units of measurement, Body fluids, Composition of the body, Nutrition, Geigy Scientific Tables (1981) 1:123-133; yamada, Tadataka (ed.), "Text book of Gastroenterology", Volume 1, Lippincott Williams & Wilkens, 1999, p 284-285). The model was simulated in vitro and the buffer was added to the basal SGF medium containing 9.6 ml of 0.1N HCl+210 ml of water and titrated with excess acid (0.1N HCl) at the rate of 0.5 ml/minute for a period of 1 hour (total volume=250 ml). The buffer(s) which maintained a pH above 6.0 at the excess secretion of acid was selected.

Figure 1B:
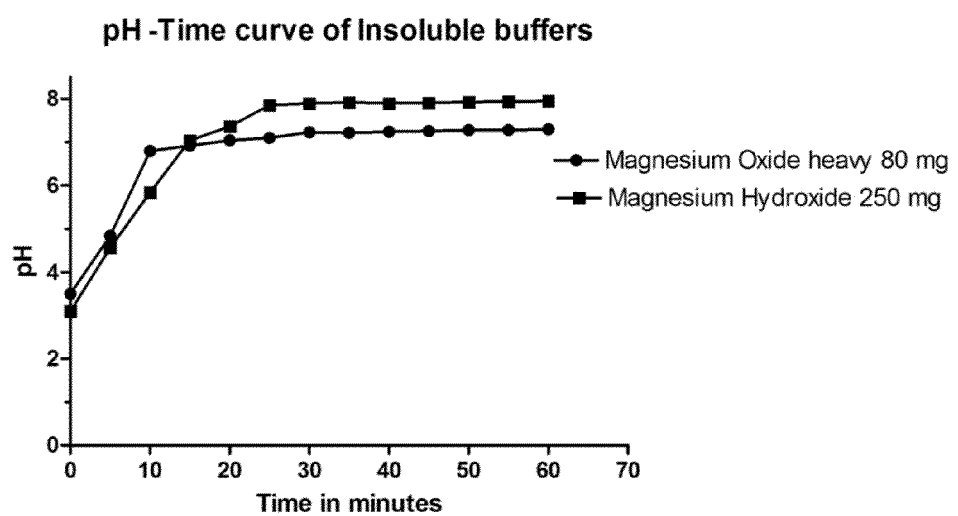
Figure 1C:
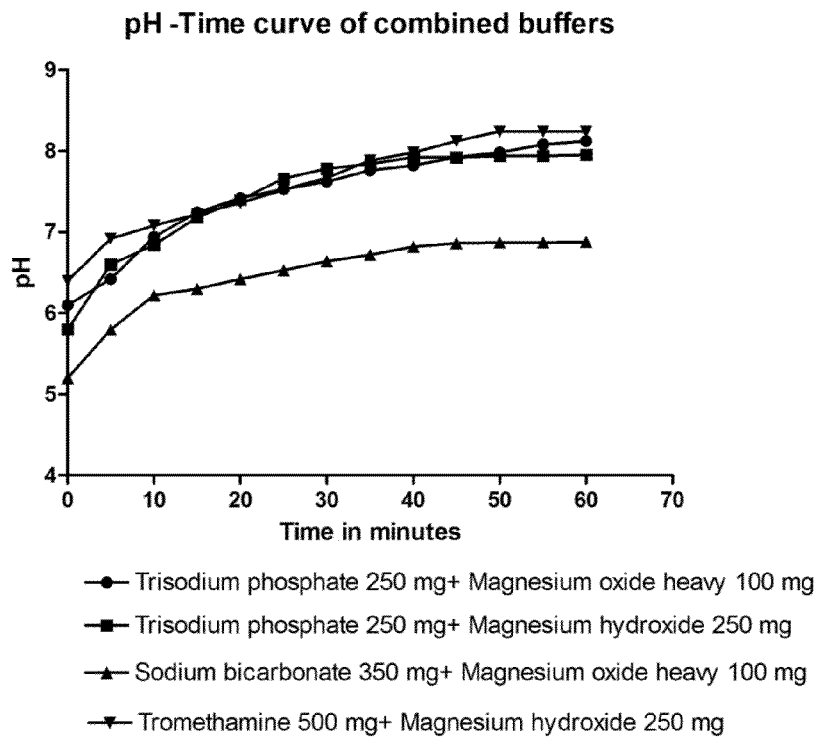

Observation:

From the FIGS. 1a to 1c the following observations were made.

1. Trisodium phosphate—About 160 mg of this buffer was required to neutralize the basal SGF which gives an initial rise in pH above 7, but upon addition of excess acid for a period of 1 h, the pH goes down to 1.7. When the buffer quantity was increased to 250 mg, it gives an initial rise in pH above 7 but upon addition of excess acid for a period of 1 h, the pH goes down to 4.5.

2. Calcium carbonate—About 280 mg of this buffer was required to neutralize the basal SGF which gives an initial rise in pH to 8, but upon addition of excess acid for a period of 1 h, the pH goes down to 3.2.

3. Sodium bicarbonate—About 350 mg of this buffer was required to neutralize the basal SGF which gives an initial rise in pH to 8, but upon addition of excess acid for a period of 1 h, the pH goes down below 5.

4. Tromethamine (TRIS buffer)—About 1000 mg of this buffer was required to neutralize the basal SGF which gives an initial rise in pH to 8 and maintains a constant pH of 8 upon addition of excess acid for a period of 1 h.

5. Heavy Magnesium oxide—About 80 mg of this buffer was required to neutralize the basal SGF which gives a rise in pH to 7 and maintains a constant pH of 7 upon addition of excess acid for a period of 1 h.

6. Magnesium hydroxide—About 250 mg of this buffer was required to neutralize the basal SGF which gives a rise in pH above 8 and maintains a constant pH of 8 upon addition of excess acid for a period of 1 h.

Based on the observations, a combination of soluble and insoluble buffers were tried to maintain the pH above 6.0. The following combinations were selected to determine the acid neutralizing capacity.

1. TSP and MgO—About 250 mg of TSP and 100 mg of MgO was required to neutralize the SGF which gives an initial rise in pH above 6, and upon addition of excess acid for a period of 1 h, the pH gradually increases and maintains a stable pH between 7.0-8.0 which proved that this combination, provides a gradual and stable rise in pH and also such an effect is produced by a minimum quantity of buffer, making it one of the suitable combinations.

2. TSP and MgOH2—About 250 mg of TSP and 250 mg of MgOH2 was required to neutralize the SGF which gives an initial rise in pH above 5.5, and upon addition of excess acid for a period of 1 h, the pH gradually increases and maintains a stable pH of 8.0, thereby rendering it as another combination suitable for use in a composition.

3. NaHCO3 and MgO—About 100 mg of MgO and 350 mg of NaHCO3 was required to neutralize the SGF which gives an initial rise in pH to 6.0, and upon addition of excess acid for a period of 1 h, the pH gradually increases and maintains a stable pH of 6.80, thereby proving that this buffer can also be used to protect the molecule from degradation.

4. Tris and MgOH2—About 250 mg of MgOH2 and 500 mg of TRIS was required to neutralize the SGF which gives an initial rise in pH to 7.0, and upon addition of excess acid for a period of 1 h, the pH gradually increases and maintains a stable pH of 8.20 which proved that this buffer can also be used to protect the molecule from degradation.

Based on compatibility of buffer with drug, release of drug in SGF in the presence of buffer, impurity profiling of the formulation with different buffers, minimum quantity of buffer required to neutralize the stomach acid and stability of the formulation, a combination of TSP and MgO was selected in the final formulation. Reference is made to FIG. 1a wherein the neutralizing capacity of soluble buffers with respect to time and pH for some embodiments. Reference is also made to FIG. 1b wherein the neutralizing capacity of insoluble buffers with respect to time and pH for some embodiments. Reference is also made to FIG. 1c wherein the neutralizing capacity of soluble buffers in combination with insoluble buffers with respect to time and pH for some embodiments.

Example 2

Effect of Various Disintegrants and Soluble Sugars on Disintegration of Buffers in 0.1N HCl The selected combination of buffers, such as magnesium oxide heavy and trisodium phosphate (MgO and TSP), magnesium hydroxide and trisodium phosphate (MgOH2 and TSP), sodium bicarbonate and magnesium oxide heavy (NaHCO3 and MgO), tromethamine and magnesium hydroxide (Tris and MgOH2) were compressed into tablets and the disintegration of these buffers as such was tested in 0.1N HCl. All the buffers were sifted through suitable mesh and mixed together in a suitable mixer. The resultant powder mix was mixed with magnesium stearate. The final blend is compressed into tablets using rotary press fitted with 11.0 mm punches. The tablets were subjected for disintegration studies.

Various disintegrants such as the croscarmellose sodium, sodium starch glycolate, crospovidone were added to the buffer blend to evaluate the disintegration of buffering agents. Alternatively, soluble sugars such as the mannitol and sucrose were also tried to enhance the release of buffering agents in acid medium.

It was observed that the compacted buffer granules compressed into tablets did not disintegrate within 10 minutes and formed lumps when exposed to acid medium which resulted in poor acid neutralization; and that may lead to degradation of the active. In order to solve this problem, formulations were prepared with several disintegrants such as the croscarmellose sodium, sodium starch glycolate and crospovidone and subjected to disintegration studies to enhance the release of buffering agents. But the disintegration results showed that the release rate of buffering agents was retarded when compared to the formulations that do not contain any superdisintegrant which might be associated with formation of gel like mass in acid medium. This phenomena was identified by the inventors which is contrary to the prior art. To enhance the disintegration rate of the buffering agents, soluble sugars such as mannitol and sucrose were added to the composition and tested for disintegration. This resulted in an immediate disintegration of buffers in acid medium which ultimately lead to attain the pH sufficient to protect the active from degradation.

TABLE 1

Effect of various disintegrants and soluble sugars on disintegration of buffers in 0.1N HCl

| S. No. | Buffer Formula | Description | Disintegration results |
|---|---|---|---|
| 1. | BF1 | TSP(250 mg) + MgO (100 mg) + magnesium stearate (3 mg) | 8.0 minutes |
| 2. | BF2 | TSP(250 mg) + MgOH2 (250 mg) + magnesium stearate (3 mg) | 10.0 minutes |
| 3. | BF3 | NaHCO3 (350 mg) + MgO (100 mg) + magnesium stearate (3 mg) | 15.0 minutes |
| 4. | BF4 | TRIS(500 mg) + MgOH2 (250 mg) + magnesium stearate (3 mg) | 16.0 minutes |
| 5. | BF5 | TSP(250 mg) + MgO (100 mg) + magnesium stearate (3 mg) + croscarmellose sodium (50 mg) | Fails. Lumps observed even after 30 minutes. |
| 6. | BF6 | TSP(250 mg) + MgO (100 mg) + magnesium stearate (3 mg) + croscarmellose sodium (100 mg) | Fails. Lumps observed even after 30 minutes. |
| 7. | BF7 | TSP(250 mg) + MgO (100 mg) + magnesium stearate (3 mg) + crospovidone (100 mg) | Fails. Lumps observed even after 30 minutes. |
| 8. | BF8 | TSP(250 mg) + MgO (100 mg) + magnesium stearate (3 mg) + sodium starch glycolate (100 mg) | Fails. Gel like mass observed even after 30 minutes. |
| 9. | BF9 | TSP(250 mg) + MgO (100 mg) + magnesium stearate (3 mg) + mannitol (100 mg) | 1.5 minutes |
| 10. | BF10 | TSP(250 mg) + MgOH2 (250 mg) + magnesium stearate (3 mg) + mannitol (100 mg) | 2.5 minutes |
| 11. | BF11 | NaHCO3 (350 mg) + MgO (100 mg) + magnesium stearate (3 mg) + mannitol (100 mg) | 4.5 minutes |
| 12. | BF12 | TRIS(500 mg) + MgOH2 (250 mg) + magnesium stearate (3 mg) + mannitol (100 mg) | 4 minutes |
| 13. | BF13 | TSP(250 mg) + MgO (100 mg) + magnesium stearate (3 mg) + sucrose (100 mg) | 2.0 minutes |
| 14. | BF14 | TSP(250 mg) + MgOH2 (250 mg) + magnesium stearate (3 mg) + sucrose (100 mg) | 3.0 minutes |
| 15. | BF15 | NaHCO3 (350 mg) + MgO (100 mg) + magnesium stearate (3 mg) + sucrose (100 mg) | 5.0 minutes |

TABLE 1-continued

Effect of various disintegrants and soluble sugars on disintegration of buffers in 0.1N HCl

| S. No. | Buffer Formula | Description | Disintegration results |
|---|---|---|---|
| 16. | BF16 | TRIS(500 mg) + MgOH2 (250 mg) + magnesium stearate (3 mg) + mannitol (100 mg) | 5.0 minutes |

The examples clearly shows that the inclusion of superdisintegrant conversely retards the release of buffering agents which might be associated with formation of gel like mass in acid medium and the same is observed when the formulation subjected for dissolution studies.

Example 3

Dissolution Studies with Buffers

The selected combination of buffers, such as magnesium oxide heavy and trisodium phosphate (MgO and TSP), magnesium hydroxide and trisodium phosphate (MgOH2 and TSP), sodium bicarbonate and magnesium oxide heavy (NaHCO3 and MgO), tromethamine and magnesium hydroxide (Tris and MgOH2), and mannitol were sifted through suitable mesh and mixed together in a suitable mixer. The resultant powder mix was lubricated with magnesium stearate. The final blend is compacted and sized through 20 mesh sieve (Endecotts Ltd., England). The resultant buffer granules were filled in capsules or compressed into tablets and the dissolution of these buffers was tested in simulated gastric fluid. The capsules/tablets were subjected for dissolution using a USP Type-I dissolution apparatus. The dissolution media consisted of 250 mL of SGF (40 mL of 0.1N HCl+210 mL of purified water; pH 1.70). The baskets were operated at 100 rpm and the bath temperature was maintained at 37±0.5° C. using a temperature controller. A pH meter was attached to one of the dissolution vessel to continuously monitor the change in pH with time and evaluated for 30 minutes.

Figure 2:
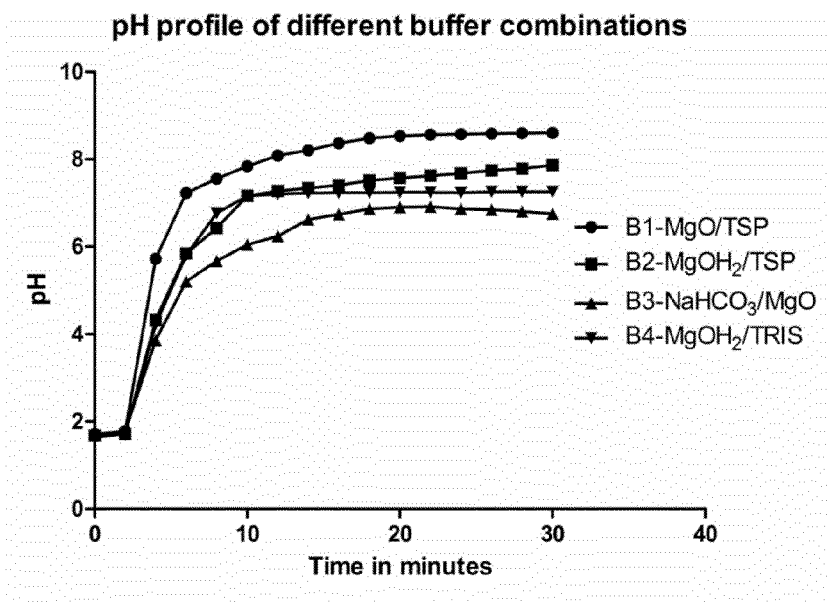
FIG. 2 illustrates the pH profile of different buffer combinations in SGF.

FIG. 2 shows the increase in pH with time on dissolution of different combination of buffers in SGF. The buffer combination which gave an immediate rise in pH and able to sustain pH of the medium above 6.0 with time, compatibility of buffer with drug and minimum quantity of buffer required to neutralize the stomach acid are important attributes of the buffer selection. A combination of MgO/TSP proved to be the best candidate for buffer selection.

Reference is made to FIG. 2 wherein the pH profile is of different buffer combinations in SGF for some embodiments.

Example 4

Dissolution Studies of the Active Pharmaceutical Ingredient (API) with and without Buffers The release profile of the Active Pharmaceutical Ingredient (API) with selected buffers from Example 3 was tested against API without buffers. The API without buffers when added to the dissolution vessel containing simulated gastric fluid, the active ingredient degraded immediately. When the API and required amount of buffer was added simultaneously to the dissolution vessel containing SGF, the active ingredient again degraded immediately; indicating that the microenvironment is not sufficient to protect the drug. When the required amount of buffers was added initially to the medium and neutralized for 2 minutes followed by the addition of accurately weighed amount of API did not result in any color change of the solution and thereby no degradation (FIG. 3).

Figure 3:
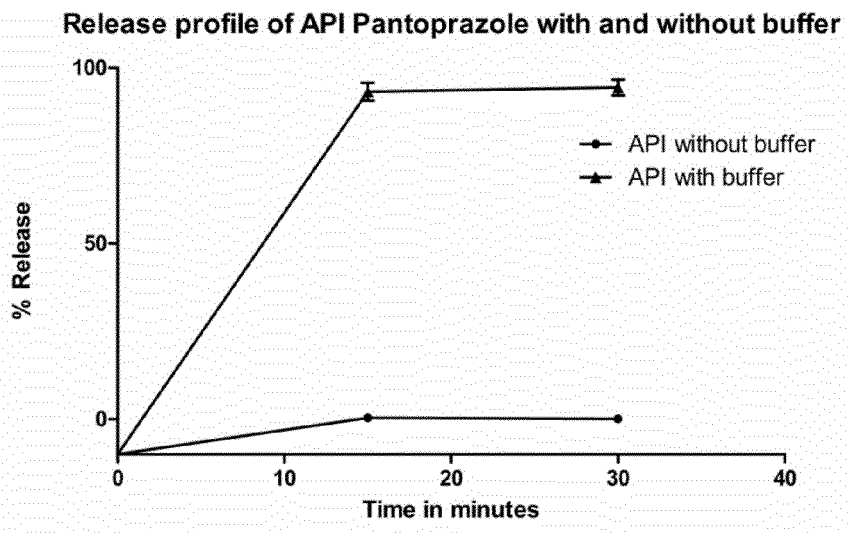
FIG. 3 illustrates the release profile of the Active Pharmaceutical Ingredient with and without buffer.

Reference is made to FIG. 3 wherein the release profile if of the active ingredient with and without buffers for some embodiments.

Example 5

Preparation of Pantoprazole Immediate Release Formulation

Example 5.1

Composition of Tablet and Buffer Granules Filled into Capsule

| Component 1: Composition of tablet to be filled into capsule | |
|---|---|
| Ingredient | mg per tablet |
| Pantoprazole sodium sesquihydrate eq. to 40 mg of pantoprazole | 45.1 |
| Crospovidone NF | 8 |
| Sodium carbonate | 15 |
| Mannitol | 28.4 |
| Colloidal silicon dioxide | 0.5 |
| Magnesium stearate | 3 |
| Total weight | 100 mg |

| Component 2: Composition of fast releasing buffer granules to be filled into capsule | |
|---|---|
| Ingredient | mg per capsule |
| Trisodium phosphate | 250 |
| Magnesium oxide heavy | 100 |
| Mannitol | 100 |
| Magnesium stearate | 3 |
| Total weight | 453 mg |

Procedure:

Pantoprazole sodium sesquihydrate, mannitol and sodium carbonate were passed through suitable mesh and mixed together. The resultant powder mix was mixed with colloidal silicon dioxide and magnesium stearate. The Lubricated Powder mix was compressed into tablet cores. Trisodium phosphate, magnesium oxide heavy and mannitol were passed through suitable mesh and mixed together. The resultant powder mix was mixed with magnesium stearate. The lubricated powder mix was subjected to slugging process and milled to produce suitable size granules. Weighed amount of buffer component and a core tablet was filled into Hydroxy propylmethyl cellulose capsules.

Example 5.2

Composition of Pellets and Buffer Granules Filled into Capsule

| Component 1: Composition of pellets to be filled into capsule | |
|---|---|
| Ingredient | mg per capsule |
| Pantoprazole sodium sesquihydrate eq. to 40 mg of Pantoprazole | 45.1 |
| Polyethylene glycol 8000 | 29.9 |
| Total weight | 75 mg |

| Component 2: Composition of fast releasing buffer granules to be filled into capsule | |
|---|---|
| Ingredient | mg per capsule |
| Trisodium phosphate | 250 |
| Magnesium oxide heavy | 100 |
| Mannitol | 100 |
| Magnesium stearate | 3 |
| Total weight | 453 mg |

Procedure:

Pantoprazole sodium sesquihydrate, polyethylene glycol 8000 were passed through suitable mesh and mixed together. The powder mix was kept in a suitable container and melt granulated to get suitable sized pellets. Weighed amount of buffer component and pellets were filled into hydroxy propylmethyl cellulose capsules.

Example 5.3

Composition of Inlay Tablet (Dual Core Tablets)

| Component 1: Composition of inner core of the tablet | |
|---|---|
| Ingredient | mg per tablet |
| Pantoprazole sodium sesquihydrate eq. to 40 mg of pantoprazole | 45.1 |
| CrospovidoneNF | 8 |
| Sodium carbonate | 15 |
| Mannitol | 28.4 |
| Colloidal silicon dioxide | 0.5 |
| Magnesium stearate | 3 |
| Total weight | 100 mg |

| Component 2: Composition of fast releasing outer core of the tablet | |
|---|---|
| Ingredient | mg per tablet |
| Trisodium phosphate | 250 |
| Magnesium oxide heavy | 100 |
| Mannitol | 200 |
| Hydroxy propyl cellulose | 50 |
| Microcrystalline cellulose | 190 |
| Colloidal silicon dioxide | 4 |
| Magnesium stearate | 6 |
| Total weight | 800 mg |

Procedure:

Pantoprazole sodium sesquihydrate, mannitol and sodium carbonate were passed through suitable mesh and mixed together. The resultant powder mix was mixed with colloidal silicon dioxide and magnesium stearate. The Lubricated Powder mix was compressed into tablet cores. Trisodium phosphate, magnesium oxide heavy, microcrystalline cellulose, hydroxy propyl cellulose and mannitol were passed through suitable mesh and mixed together. The resultant powder mix was mixed with magnesium stearate. The Lubricated Powder mix was subjected for slugging process and milled to produce suitable size granules. 200 mg of the buffer composition was filled into die cavity of the rotary press and core tablet placed at the center and remaining 600 mg buffer composition filled over that and compressed into tablet.

Example 6

Preparation of Rabeprazole Immediate Release Formulation

Example 6.1

Composition of Tablet and Buffer Granules Filled into Capsule

| Component 1: Composition of tablet to be filled into capsule | |
|---|---|
| Ingredient | mg per tablet |
| Rabeprazole sodium | 21.32 |
| Crospovidone NF | 6 |
| Magnesium oxide | 25 |
| Ludipress | 44.98 |
| Colloidal silicon dioxide | 0.7 |
| Magnesium stearate | 2 |
| Total weight | 100 mg |

| Component 2: Composition of fast releasing buffer granules to be filled into capsule | |
|---|---|
| Ingredient | mg per capsule |
| Trisodium phosphate | 250 |
| Magnesium oxide heavy | 100 |
| Mannitol | 100 |
| Magnesium stearate | 3 |
| Total weight | 453 mg |

Procedure:

Rabeprazole sodium, ludipress and magnesium oxide were passed through suitable mesh and mixed together. The resultant powder mix was mixed with colloidal silicon dioxide and magnesium stearate. The Lubricated Powder mix was compressed into tablet cores. Trisodium phosphate, magnesium oxide heavy and mannitol were passed through suitable mesh and mixed together. The resultant powder mix was mixed with magnesium stearate. The lubricated powder mix was subjected for slugging process and milled to produce suitable size granules. Weighed amount of buffer component and a core tablet was filled into hydroxy propylmethyl cellulose capsules.

Example 6.2

Composition of Inlay Tablet (Dual Core Tablets)

| Component 1: Composition of inner core of the tablet | |
|---|---|
| Ingredient | mg per tablet |
| Rabeprazole sodium | 21.32 |
| Crospovidone NF | 6 |
| Magnesium oxide | 25 |
| Ludipress | 44.98 |
| Colloidal silicon dioxide | 0.7 |
| Magnesium stearate | 2 |
| Total weight | 100 mg |

| Component 2: Composition of fast releasing outer core of the tablet | |
|---|---|
| Ingredient | mg per tablet |
| Trisodium phosphate | 250 |
| Magnesium oxide heavy | 100 |
| Mannitol | 200 |
| Hydroxy propyl cellulose | 50 |
| Microcrystalline cellulose | 190 |
| Colloidal silicon dioxide | 4 |
| Magnesium stearate | 6 |
| Total weight | 800 mg |

Procedure:

Rabeprazole sodium, ludipress and magnesium oxide were passed through suitable mesh and mixed together. The resultant powder mix was mixed with colloidal silicon dioxide and magnesium stearate. The Lubricated Powder mix was compressed into tablet cores. Trisodium phosphate, magnesium oxide heavy, microcrystalline cellulose, hydroxy propyl cellulose and mannitol were passed through suitable mesh and mixed together. The resultant powder mix was mixed with magnesium stearate. The Lubricated Powder mix was subjected for slugging process and milled to produce suitable size granules. 200 mg of the buffer composition was filled into die cavity of the rotary press and core tablet placed at the center and remaining 600 mg buffer composition filled over that and compressed into tablet.

Example 7

Figure 4:
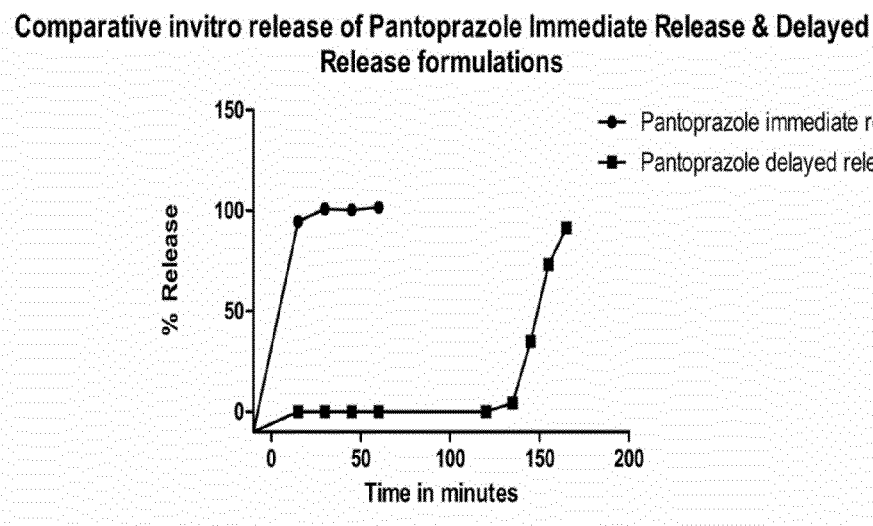
FIG. 4 illustrates the In vitro dissolution profile of the immediate release composition of the present invention in comparison to a marketed delayed release formulation.

Dissolution Studies of the Composition in Comparison to Innovators Delayed Release Formulation The composition of the present invention was formulated as disclosed above. A comparative in-vitro release profile of the innovators delayed release formulation and the proposed immediate release formulation was evaluated. The release profile of the composition of the present invention was tested in simulated gastric fluid medium (40 mL of 0.1N HCl+210 mL of water, pH=1.70). About 95% of the active ingredient was released in 15 minutes and 100% was released in 30 minutes (FIG. 4). The Innovators formulation was tested in acid medium for 2 h followed by dissolution in intestinal pH to simulate invitro. The delayed release formulation releases only 90% at the end of 3 h in intestinal pH.

Reference is made to FIG. 4 wherein the comparative dissolution profile of the proposed IR composition and innovators delayed release composition for some embodiments.

Example 8

Application of Micro Environment pH and Macro Environment pH Concept to the Proposed Invention For illustration the formula (Example 5.1) was prepared as per the microenvironment pH concept (as per prior art) (the API and excipients were granulated and filled into capsules) and added to the dissolution vessel containing SGF, the color of the medium changed immediately and did not give an initial rise in pH thereby leading to partial degradation of the API in the medium which indicates that the microenvironment pH was too low to protect the drug from degradation. But on the other hand when the same formula (Example 5.1) was prepared as per the macroenvironment pH concept (as per the present invention) and added to the dissolution vessel containing SGF, a pH raise in the medium was observed within 4 minutes and as a result the API did not degrade. It is evident from the data that the micro environment pH concept retards the release of the drug and generates more impurities in contrary to the macro environment pH concept.

TABLE 2

Dissolution and Related impurities of the Immediate release composition using micro environment pH and macro environment pH concept

| | Panto IR capsules | |
|---|---|---|
| Tests | Micro environment pH | Macro environment pH |
| Dissolution at 30 min (%) | 86.1 | 102.1 |
| Related Impurities (%) | 4.82 | 0.43 |

Figure 5:
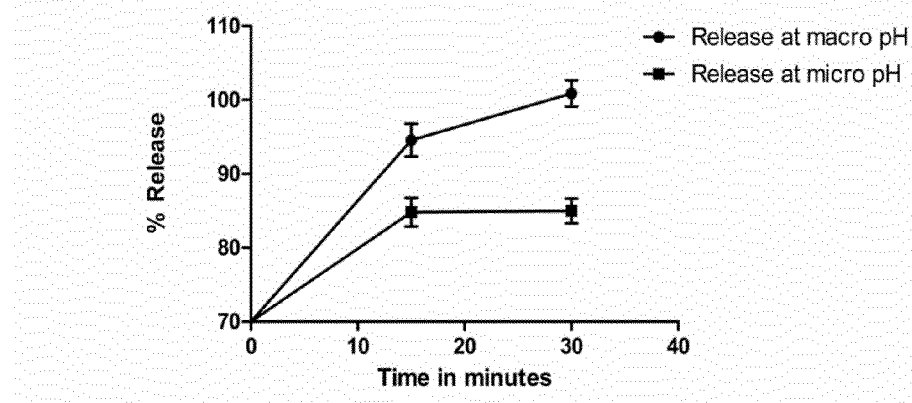
FIG. 5 illustrates the Comparative in vitro release of drug from immediate release formulation illustrating microenvironment and macroenvironment pH concept.

Reference is also made to FIG. 5 wherein the figure illustrates the comparative in vitro release of drug from immediate release formulation illustrating microenvironment and macroenvironment pH concepts for some embodiments.

Example 9

Stability Profile of the Proposed Composition

The selected formula (Example 5.1, 5.2 & 5.3) was employed to prepare the final compositions and subjected to stability studies as per the ICH guidelines. The samples were subjected to 30° C./65% RH for long term storage and 40° C./75% RH for accelerated storage. Since the product is highly sensitive to moisture the samples were packaged in alu-alu blisters. The product kept at stability was evaluated for assay, related substances and dissolution and compared with initial room temperature (RT) results. The results were promising with fewer amounts of related substances and a good release pattern which is comparable with RT results is summarized in Table 3 below.

TABLE 3

Stability data of Pantoprazole Immediate Release composition

| Tests | Stability storage condition | Tab-in-cap | | | Tab-in-tab | | | Pellets-in-cap | | |
|---|---|---|---|---|---|---|---|---|---|---|
| | | Initial | 3M | 6M | Initial | 3M | 6M | Initial | 3M | 6M |
| Pantoprazole (40 mg/cap) | 30° C./65% RH | 102.40 | 102.76 | 102.21 | 100.58 | 99.65 | 99.54 | 99.02 | 99.42 | 98.35 |
| | 40° C./75% RH | 102.40 | 101.76 | 101.06 | 100.58 | 98.78 | 98.80 | 99.02 | 98.74 | 97.56 |
| Dissolution | 30° C./65% RH | 101.24 | 101.78 | 101.82 | 99.87 | 99.35 | 98.56 | 96.90 | 98.54 | 97.20 |
| | 40° C./75% RH | 101.24 | 101.20 | 100.50 | 99.87 | 98.52 | 97.44 | 96.90 | 95.20 | 96.32 |
| Related impurities | 30° C./65% RH | 0.09 | 0.12 | 0.23 | 0.10 | 0.14 | 0.30 | 0.18 | 0.26 | 0.40 |
| | 40° C./75% RH | 0.09 | 0.18 | 0.26 | 0.10 | 0.20 | 0.34 | 0.18 | 0.32 | 0.48 |

Example 10

Comparative Bioavailability of Pantoprazole Immediate Release Vs Delayed Release Formulation in Healthy Adult Subjects Purpose:

To determine and compare the bioavailability of the new pantoprazole immediate release formulation administered in single dose relative to the marketed tablet. Pantoprazole is a proton pump inhibitor indicated for the treatment of gastro esophageal reflux disease. The new formulation was developed in order to overcome the disadvantages of delayed release formulations which have a delayed Tmax and hence delayed effect.

Study Design:

An open label, single dose, randomized, two-treatment, two-period, two-sequence, fasting, crossover pilot comparative bioavailability study with a washout period of one week between doses.

Methods:

This was a randomized, open-label, 2-period, 2-treatment, 2-sequence, fasting, single-dose, crossover comparative bioavailability study with a washout period of one week between doses in 12 healthy adult subjects. Each subject received 40 mg of either test or reference Pantoprazole tablet in each of the 2 study periods. Blood samples were collected up to 24 hours post dose and analyzed for Pantoprazole by a validated HPLC method. Standard safety evaluations were performed. The PK parameters were estimated using non-compartmental methods. The 90% confidence limits for the test-to-reference geometric mean ratio were calculated for Cmax, Tmax and AUC.

Study Design:

Healthy adult Caucasian participants ages between 18 and 50 years, body-mass index 19 to 30 kg/m2 inclusive, non-smokers or moderate smokers (smokers of less than 10 cigarettes per day) participated in the study after providing written informed consent. All were judged to be healthy and were not receiving any medication during the study period. The protocol used was a conventional, two-way, split group, crossover study with 6 subjects in each of the two treatment groups. In the first trial period, each volunteer of group 1 was given one capsule of pantoprazole IR while those of group 2, one tablet of pantoprazole DR. After a washout period of one week, each volunteer then received the alternate product. Both products were administered in the morning (08.00 am) with 240 ml of water after an overnight fast. Blood samples of (16 mL) pre-dose and (8 mL) at 0.25, 0.50, 0.75, 1.00, 1.25, 1.50, 1.75, 2.00, 2.25, 2.50, 2.75, 3.00, 3.33, 3.67, 4.00, 4.50, 5.00, 5.50, 6.00, 7.00, 8.00, 10.0, 12.0, 14.0, and 16.0 hours post-dose were collected. The total number of blood samples in each study period will be 26. The blood samples were collected via indwelling catheter into the labeled heparin blood tubes (10.0 mL) and centrifuged (4000 rpm/4.0 minutes). The plasma samples were transferred, using disposable polypropylene droppers into the labeled polypropylene tubes containing a base to increase the plasma pH to ≥8, then capped and stored at −80° C. until analysis.

Comment and Conclusion:

This relative bioavailability study was conducted to evaluate an immediate release product of pantoprazole relative to the delayed release product. The results of this study showed that the immediate release product had relative bioavailability of above 80% AUC ratio. The ratio of Cmax was also more than 80%. The idea of immediate release was proved in this study by the fact that the maximum concentration for the immediate release product was at 0.75 hour compared to 2.63 hours for the delayed release product.

Moreover, the test product showed a uniform Tmax of 0.75 h for all the 12 volunteers whereas the reference product Tmax showed a wide variation between 1.75 h to 4.50 h for the 12 volunteers, which could be due to non uniform disruption of enteric coating and hence a wide variability in release of the dosage form. This proves that the immediate release formulation is advantageous over the delayed release formulation. As a conclusion, the immediate release product of pantoprazole achieved its goal in providing pantoprazole a significantly shorter time and at the same time the relative bioavailability was more than 80%.

Figure 6:
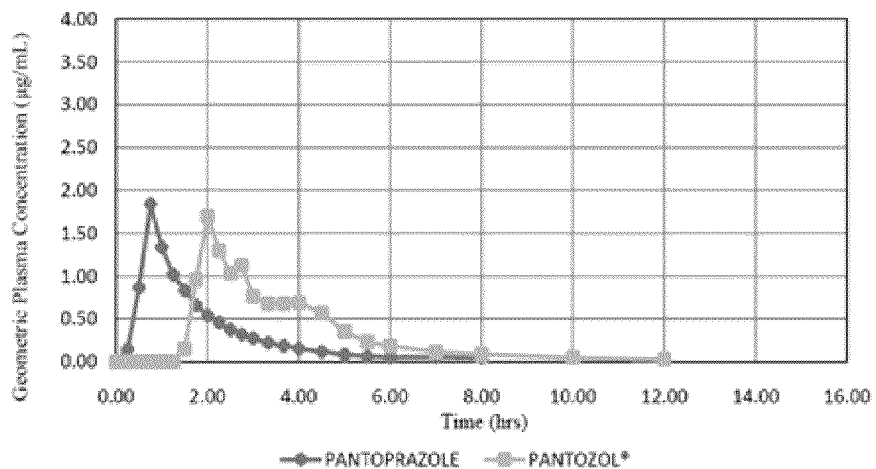
FIG. 6 illustrates the bioavailability of a composition of the present invention in comparison to a marketed formulation.

Reference is made to FIG. 6 for the comparison of a composition of the present invention to a marketed formulation for some embodiments.

We claim:

1. A method of creating a macro environment having a pH in the range of 5 to 10 in the stomach for immediate release of an active ingredient comprising the step of administering a composition comprising first and second components;

the first component comprising the active ingredient selected from an acid labile compound stable at a pH between 5 to 10 or an alkali soluble compound, in a core, further comprising a stabilizing agent, lubricant, and other pharmaceutically acceptable excipients;

the second component comprising a water-soluble buffer, a water-insoluble buffer, a disintegrant and pharmaceutically acceptable excipients;
wherein the disintegrant is a polyol or sugar and excludes super disintegrants selected from crocarmellose sodium, crospovidone, and sodium starch glycolate.

2. The method of claim 1, wherein the pH of the macro environment between 5 to 10 is created within 20 minutes after disintegration of the composition.

3. The method of claim 1 wherein the pH of the macro environment is maintained above 5 for at least 15 minutes.

4. The method of claim 1, wherein the active ingredient is released within 30 minutes.

5. The method of claim 1 wherein the disintegration of the composition begins within 15 minutes.

6. The method of claim 1, wherein the dissolution rate of the composition is about 95% within 15 minutes and about 100% within 30 minutes.

7. The method of claim 1, wherein the alkali soluble compound is selected from the group consisting of COX-2 inhibitors, antidiabetics, retinoids, and other drugs soluble at alkaline pH or near alkaline pH as free base, free acid, salt, hydrate, polymorph, or prodrug.

8. The method of 1, wherein the acid labile compound is a prazole.

9. The method of claim 8, wherein the prazole is selected from the group consisting of omeprazole, pantoprazole, rabeprazole, esomeprazole, and lansoprazole.

10. The method of claim 1, wherein the water-soluble buffer is selected from the group consisting of meglumine, sodium bicarbonate, sodium carbonate, sodium citrate, calcium gluconate, disodium hydrogen phosphate, dipotassium hydrogen phosphate, tripotassium phosphate, trisodium phosphate, sodium tartarate, sodium acetate, calcium glycerophosphate, tromethamine, and combinations thereof.

11. The method of claim 1, wherein the water-soluble buffer is trisodium phosphate.

12. The method of claim 1, wherein the water-insoluble buffer is selected from the group consisting of magnesium hydroxide, aluminum hydroxide, dihydroxy aluminum sodium carbonate, calcium carbonate, calcium hydroxide, aluminum phosphate, aluminum carbonate, dihydroxy aluminum amino acetate, magnesium oxide, magnesium trisilicate, magnesium carbonate, and combinations thereof.

13. The method of claim 1, wherein the water-insoluble buffer is magnesium oxide.

14. The method of claim 1, wherein the water-soluble buffer is present in the range of 50 mg and 1000 mg.

15. The method of claim 1, wherein the water-insoluble buffer is present in the range of 20 mg and 1000 mg.

16. The method of claim 1, wherein the polyol or sugar is selected from the group consisting of mannitol, sorbitol, xylitol, lactitol, erythritol, maltitol, and combinations thereof.

17. The method of claim 1, wherein the sugar is selected from the group consisting of sucrose, Alveo sugar, castor sugar, and icing sugar.

18. The method of claim 1, wherein the disintegrant is mannitol.

19. The method of claim 1, wherein the disintegrant is present in the range of 5% to 50% w/w of the total composition.

20. The method of claim 1, wherein the pharmaceutically acceptable excipients comprise stabilizing agent, cellulose derivative, fillers, glidants, binder, colorants, flavorants, and sweetening agents.

21. The method of claim 1 in the form of a inlay tablet, inlay caplet, multilayered tablet, multilayered caplet, mixture of pellets compressed into tablet, mixture of pellets filled into capsule, pellets and granules compressed into tablet, mini tablets filled into capsule, tablet and powder filled into capsule, tablet and granular powder filled into capsule, pellets and powder filled into capsule, and pellets and granular powder filled into capsule.

22. A process for preparing an oral dosage form comprising the composition of claim 1, wherein
a. the buffer of the composition is released first;
b. the buffer achieves a pH of 5 to 10 in the stomach;
c. the active ingredient is released after the pH of 5 to 10 is achieved.

23. A pharmaceutical composition for immediate release of acid labile compounds comprising first and second components, the first component comprising an active ingredient selected from an acid labile compound stable at pH between 5 to 10 or an alkali soluble compound, in a core, further comprising a stabilizing agent, lubricant, and other pharmaceutically acceptable excipients; and the second component comprising a water-soluble buffer, a water-insoluble buffer, a disintegrant, and pharmaceutically acceptable excipients, wherein the disintegrant is a polyol or sugar and excludes super disintegrants selected from crocarmellose sodium, crospovidone, and sodium starch glycolate.

24. The pharmaceutical composition of claim 23, wherein the disintegration of the composition begins within 15 minutes.

25. The pharmaceutical composition of claim 23, wherein the composition achieves a dissolution of about 95% within 15 minutes and about 100% in 30 minutes.

26. The pharmaceutical composition of claim 23, wherein the alkali soluble compound is selected from the group consisting of COX-2 inhibitors, antidiabetics, retinoids, and other alkali soluble drugs soluble at alkaline pH or near alkaline pH as free base, free acid, salt, hydrate, polymorph or prodrug.

27. The pharmaceutical composition of claim 23, wherein the acid labile compound is a prazole.

28. The pharmaceutical composition of claim 23, wherein the water soluble buffer is selected from the group consisting of meglumine, sodium bicarbonate, sodium carbonate, sodium citrate, calcium gluconate, disodium hydrogen phosphate, dipotassium hydrogen phosphate, tripotassium phosphate, trisodium phosphate, sodium tartarate, sodium acetate, calcium glycerophosphate, tromethamine, and combinations thereof.

29. The pharmaceutical composition of claim 23, wherein the water-insoluble buffer is selected from the group consisting of magnesium hydroxide, aluminum hydroxide, dihydroxy aluminum sodium carbonate, calcium carbonate, calcium hydroxide, aluminum phosphate, aluminum carbonate, dihydroxy aluminum amino acetate, magnesium oxide, magnesium trisilicate, magnesium carbonate, and combinations thereof.

30. The pharmaceutical composition of claim 23, wherein the disintegrant is selected from the group consisting of: mannitol, sorbitol, xylitol, lactitol, erythritol, maltitol, sucrose, Alveo sugar, castor sugar, icing sugar, and combinations thereof.

31. The pharmaceutical composition of claim 23, wherein the disintegrant is present in the range of range of 5% to 50% w/w of the total composition.

32. The pharmaceutical composition of claim 23, wherein the pharmaceutically acceptable excipients comprise stabilizing agent, cellulose derivative, glidants, binder, colorants, flavourants, and sweetening agents.

33. The pharmaceutical composition of claim 23 in the form of an inlay tablet, inlay caplet, multilayered tablet, multilayered caplet, mixture of pellets compressed into tablet, mixture of pellets filled into capsule, pellets and granules compressed into tablet, mini tablets filled into capsule, tablet and powder filled into capsule, tablet and granular powder filled into capsule, pellets and powder filled into capsule, and pellets and granular powder filled into capsule.

34. The pharmaceutical composition of claim 27 wherein the prazole is selected from the group consisting of omeprazole, pantoprazole, rabeprazole, esomeprazole, and lansoprazole.

\* \* \* \* \*